United States Patent [19]
Hughes et al.

[11] 3,976,787
[45] Aug. 24, 1976

[54] PHARMACEUTICAL GUANIDINE PREPARATIONS AND METHODS OF USING SAME

[75] Inventors: John Lawrence Hughes; Robert Chung-Huan Liu, both of Kankakee; Takashi Enkoji; James Winslow Bastian, both of Park Forest, all of Ill.

[73] Assignee: Armour Pharmaceutical Company, Phoenix, Ariz.

[22] Filed: Mar. 6, 1975

[21] Appl. No.: 556,067

Related U.S. Application Data

[63] Continuation-in-part of Ser. No. 88,501, Nov. 10, 1970, abandoned.

[52] U.S. Cl. ................................................ 424/326
[51] Int. Cl.² ........................................ A61K 31/155
[58] Field of Search ..................................... 424/326

[56] References Cited
UNITED STATES PATENTS
3,681,459  8/1972  Hughes et al. ..................... 424/326

OTHER PUBLICATIONS
Dawes et al., Brit. J. Pharmac., (1950), vol. 5, pp. 65–76.

Okujima, Chemical Abstracts, 47:3923(c), (1953).

*Primary Examiner*—Norman A. Drezin
*Attorney, Agent, or Firm*—Richard R. Mybeck

[57] ABSTRACT

Pharmaceutical preparations and methods of using the same to treat a host having a condition requiring vasoconstrictive therapy. The preparations comprise a pharmaceutically acceptable carrier and a guanidine compound, or non-toxic acid addition salt thereof, having the structural notation:

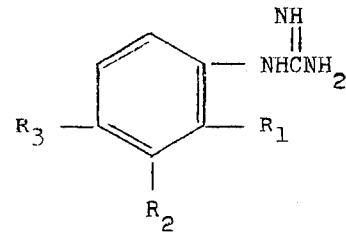

wherein: $R_1$ is hydrogen or alkyl having 1–4 carbon atoms; $R_2$ is hydrogen, hydroxy, chloro, fluoro or bromo; and $R_3$ is hydrogen or the same as $R_2$ when $R_2$ is chloro, bromo or fluoro.

12 Claims, No Drawings

PHARMACEUTICAL GUANIDINE PREPARATIONS AND METHODS OF USING SAME

RELATED APPLICATION

This application is a continuation in part of our co-pending application for United States Letters Patent Serial No. 88,501 filed Nov. 10, 1970 entitled "Pharmaceutical Preparations and Methods of Using Same", now abandoned.

DESCRIPTION OF INVENTION

This invention relates generally to methods of using and preparations containing certain guanidine compounds to realize the benefits of their newly discovered biological properties and, more particularly, to preparations containing a class of guanidine compounds and their corresponding non-toxic acid addition salts which possess vasoconstrictor properties and hence are useful as vasoconstrictor agents when formulated into pharmaceutical preparations.

The class of compounds embraced with the present invention and for which this patent is sought are represented by the structural notation:

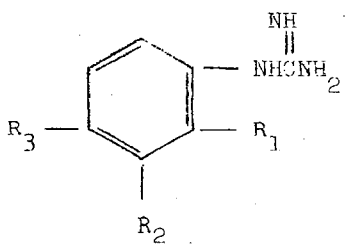

wherein: $R_1$ is hydrogen or alkyl having 1–4 carbon atoms; $R_2$ is hydrogen, hydroxy, chloro, fluoro or bromo; and $R_3$ is hydrogen or the same as $R_2$ when $R_2$ is chloro, bromo or fluoro.

Representative of compounds suitable for practice of this invention are: 3',4'-dichlorophenyl guanidine; phenyl guanidine; 3'-hydroxyphenyl guanidine; and 2'-methylphenyl guanidine. Representative of the salts embodied in this invention are: phenyl guanidine nitrate; 3'-hydroxyphenyl guanidine hydrochloride; 2'-methylphenyl guanidine nitrate; and 3',4'-dichlorophenyl guanidine hydrochloride.

The term "vasoconstrictor agent," as used herein, means an agent which is useful in treatment to effect the amelioration of congestive states of the eye and nose, and in treatment of shock and other hypotensive states.

Compounds known previously as vasoconstrictor agents, and currently marketed as such, are methoxamine, ephedrine, epinephrine, oxymetazoline, phenylephrine, levartenenol, naphazoline and tuaminoheptane.

While these compounds have been successful in providing the desired vasoconstrictive action, they have also been the cause of severe adverse reactions such as cardiac arrhythmias and excessive elevation of blood pressure. Further, such compounds, when employed in topical formulations, are known to cause stinging, burning, and the sensation of intense dryness.

The present invention is predicated upon the discovery of biological activity in the guanidine compounds, and their corresponding non-toxic acid addition salts, which are shown above, which activity resides in the remarkably unexpected properties of these compounds and the indicated salts to obtain vasoconstrictor activity without any significant changes in the cardiac rate of the host to whom such agents are administered. Further, as will appear, the preparations of this invention may be administered by oral, parenteral and topical routes with but minimal effects on the cardiac rate of the host animal, including man.

Accordingly, one of the prime objects of the present invention is to provide new pharmaceutical preparations and methods which are useful to provide vasoconstrictive therapy.

A further object of the present invention is to provide new pharmaceutical preparations containing aromatic guanidine compounds, or the corresponding non-toxic acid addition salts thereof, which can be employed as vasoconstrictor agents and are free from significant effects on the cardiac rate of the host to whom it is administered.

Still another object of the present invention is to provide new pharmaceutical preparations and methods of using them, which are useful in the treatment of hypotensive states, and as nasal and ocular decongestants.

These and still further objects as shall hereinafter appear are fulfilled by the present invention in a remarkably unobvious fashion as will be discerned from the following detailed description and examples of embodiments of this invention.

The guanidine compounds of the present invention can be prepared by any of several procedures, for example, the addition of hydrogen cyanamide to an aromatic amine (or its mineral acid addition salt).

The guanidines may be converted to their acid addition salts by reacting the selected guanidine with an appropriate mineral or organic acid such, for example, as hydrochloric, sulfuric, nitric, hydrobromic, hydroiodic, maleic, citric, acetic, tartaric, benzoic propionic, carbonic, and the like acids which are well known for their reaction to form pharmaceutically acceptable salts and do not need to be belabored here.

One suitable procedure for preparing the guanidines comprises mixing the appropriate aromatic amine mineral acid addition salt (or the aromatic amine with one molar equivalent of the appropriate mineral acid), aqueous 50% cyanamide solution and ethyl alcohol and then heating the mixture at reflux for 3 to 20 hours. For optimum yield, the molar ratio of aromatic amine salt, cyanamide, and ethyl alcohol is 1.0:1.5:15 respectively. The products, i.e., the aromatic guanidine mineral acid addition salts, are isolated from the reaction mixtures and purified by recrystallication from an appropriate solvent, i.e., water or aliphatic alcohols. When the acid addition salt cannot be purified, it is converted to the free base by the addition of an alkali hydroxide and purified by recrystallization from an appropriate solvent.

Another satisfactory method comprises forming a mixture of an appropriate 1-aryl-2-methyl-2-thiopseudourea hydroiodide, ammonia and ethyl alcohol. The mixture is heated at reflux for 20 hours. For optimum yield, the molar ratio of the thiopseudourea, ammonia and ethyl alcohol was 1:3:15, respectively. The products are isolated from their reaction mixtures and converted to hydrochloride salts for purification and characterization.

A guanidine compound, prepared by either of the foregoing procedures, or by other suitable procedures, may be converted to its acid addition salt, e.g., hydrochloride by the addition of the appropriate acid to the guanidine compound.

The guanidine compounds of this invention may be employed as free bases or in the form of their non-toxic pharmaceutically acceptable salts. Thus, for example, organic and inorganic acid addition salts may be employed, such as the salts of hydrochloric, sulfurnic, nitric, phosphoric, citric, acetic, lactic, tartaric, sulfamic, succinic, fumaric, maleic, ethanedisulfonic, hydrobromic, benzoic and similar non-toxic acids. The salts may be prepared by reacting the guanidine base with an excess of acid in a suitable solvent, such as ethanol, acetone, water, or mixture thereof. The mixture is heated to effect solution, and the salts crystallize on cooling.

The guanidines and their salts are administered in therapeutically effective amounts to animals, including man, and in appropriate ways. Thus, dosages of about 1 milligram to 5 milligrams per kilogram of host body weight may be provided to man by systemic administration, e.g., orally or parenterally. The compounds may be administered systemically to animals other than man in dosages of up to about 5 milligrams per kilogram of body weight. The foregoing and other dosage levels herein are based on the content of guanidine base. The compounds have excellent vasoconstriction, a low order of toxicity, and relatively few observed side effects.

In the preferred embodiments of the invention, an aromatic guanidine or a salt thereof is administered in a pharmaceutical composition which includes the guanidine compound and a pharmaceutical carrier. The carrier is a non-toxic pharmaceutical grade substance which may be either solid or liquid. Suitable solid carriers include lactose, magnesium stearate, starch, sucrose, mannitol, sorbitol, cellulose powder, dicalcium phosphate, talc, stearic acid, gelatin, agar pectin, acacia and the like. Suitable liquid carriers include glycols, polyglycols, dimethylsulfoxide, peanut oil, olive oil, sesame oil, alcohols, water, and the like. If desired, the carrier may include a time delay material such as glycerol mono-stearate, or glycerol di-stearate, alone or with a wax.

The composition preferably is provided in unit dosage form for accuracy and convenience in administration. Where appropriate, oral administration is effective and preferred, and dosage units suitable for oral administration are provided. Examples of such dosage units employing solid carriers include tablets, filled capsules, packets and the like, and lozenges. The amount of solid carrier per dosage unit may vary widely, preferably from about 25 milligrams to 5 gram.

The guanidines and their salts may be compounded with semi-solid and liquid carriers in solutions, suspensions, emulsions, ointments, suppositories and soft gelatin capsules, for example. Such compositions may be administered pancavally, i.e., via natural and artificial openings in the body, such as the mouth, the anus, the vagina, the nares, and the stoma of colostomy patients, intravenously or intramuscularly, employing the appropriate composition having a suitable concentration of active ingredient according to the desired route of administration.

The foregoing dosage forms are prepared by conventional procedures of mixing, granulating, compressing, suspending and/or dissolving, as is suitable to prepare the desired dosage form.

The vasoconstriction of a host animal, including man, which has a condidtion requiring such treatment is readily obtained by administering to the afflicted host an aromatic guanidine or a pharmaceutically acceptable acid addition salt thereof in an amount sufficient to alleviate the symptoms of the condition. The usual symptoms requiring treatment are low blood pressure, ocular and nasal congestion, and the like.

The compound preferably is administered at the dosage level described above and preferably in a pharmaceutical carrier. The dosage level and frequency of administration are to a certain extent subjective, attention being given to the degree of vasoconstriction or decongestion, the case history, the reaction of the subject, and the like.

The daily dosage can be administered in one or more parts and the administration can be accomplished pancavally or parenterally or topically. Administration for the provision of systemic vasoconstriction is preferably oral and is most conveniently accomplished by means of a tablet containing one of the active compounds and a pharmaceutical carrier. For local vasoconstriction, that is eyes, nose, etc., topical administration is preferred.

Especially good vasoconstrictive results are obtained when administering to the animal organism the following aromatic preparations containing guanidines. Phenyl guanidine; 3'-hydroxyphenyl guanidine; 2'-methylphenyl guanidine; and 3',4'-dichlorophenyl guanidine. Representative of the salts embodied in the preparations of this invention are: phenyl guanidine nitrate; 3'-hydroxyphenyl guanidine hydrochloride; 2'-methylphenyl guanidine nitrate; and 3',4'-dichlorophenyl guanidine hydrochloride.

The onset of activity after oral administration in the animal organism is rapid, results being observed within one-half hour, and the activity is sustained. Thus, the activity levels remain high for 2 or more hours, and activity persists over a 24-hour period. After topical or intravenous administration, the onset of action is rapid and persists for one or more hours.

The following examples are illustrative of the preparation of the guanidines of the invention. The new pharmaceutical compositions embodying said guanidine and their non-toxic acid addition salts, the treatment of the animal organism in accordance with the invention, and the activities exhibited in such treatment. It is to be understood that the invention is not limited to the examples or to the compounds, compositions, proportions, conditions, and methods set forth therein, which are only illustrative. Throughout the examples, the specific guanidines enumerated have been used to typify the entire class of compounds and compositions of the invention.

EXAMPLE I

Phenyl guanidine nitrate is prepared from a mixture of 12.8 g (0.1 mole) of aniline, 9.0 g of concentrated nitric acid (equivalent to 0.1 mole of $HNO_3$), 12.6 g of a 50 percent aqueous cyanamide solution (equivalent to 0.15 mole of cyanamide) and 100 ml of ethyl alcohol which is heated under reflux for 20 hours. The reaction mixture is then cooled to 0°C for 5 hours and the precipitated product is collected on a filter. The product is purified by recrystallization from ethyl alcohol. The purified white crystalline solid melts at 125°–7°C. The infrared spectrum was consistent with the assigned structure.

EXAMPLE II

3'-hydroxyphenyl guanidine hydrochloride is prepared from a mixture of 10.9 g (0.1 mole) of 3-aminophenol, 10 g of concentrated hydrochloric acid (equivalent to 0.1 mole of HCl), 12.6 g of a 50 percent aqueous cyanamide solution (equivalent to 0.15 mole), and 100 ml of ethyl alcohol which was heated at reflux for 3 hours. The product was isolated from the reaction mixture by evaporation of the reaction solvent and trituration of the residue with acetone. The solid obtained after decantation was recrystallized from a mixture of isopropyl alcohol and acetone in a 1:2 ratio. The purified white crystalline solid melted at 155°–7°C. The infrared spectrum was consistent with the assigned structure.

Analysis - Calculated for $C_7H_{10}ClN_3O$: C, 44.81; H, 5.37; N, 22.40; Cl, 18.90. Found: C, 44.96; H, 5.52; N, 22.49; Cl, 19.02.

EXAMPLE III 2-methylphenyl guanidine is prepared by using the reaction procedure of Example I except that 2-methylaniline is used in place of the aniline. The reaction mixture was evaporated and the residue triturated with ether. The ether was decanted leaving a crystalline solid. This material was purified by recrystallization from isopropyl alcohol. The white crystalline product melted at 128°–130°C. The infrared spectrum was consistent with assigned structure.

EXAMPLE IV

3',4'-Dichlorophenyl guanidine hydrochloride is prepared using the reaction procedure of Example II except that 3,4-dichloroaniline is used in place of the 3-aminophenol and the reaction mixture reflux time is 20 hours. The reaction mixture was evaporated and the residue dissolved in boiling aqueous 2N hydrochloric acid solution. This solution was filtered and cooled to 0°C for 18 hours. The precipitated solid was collected on a filter and dried. This solid was recrystallized from isopropyl alcohol. The white crystalline solid melted at 178°–80°C. The infrared spectrum was consistent with the assigned structure.

Analysis - Calculated for $C_7H_8Cl_3N_3$: C, 34.96; H, 3.35; Cl, 44.22; N, 17.47. Found: C, 34,81; H, 3.36; Cl, 44.03; N, 17.34.

EXAMPLE V

The following are examples of several dosage forms useful for the practice of the present invention using oral administration.

FORMULATION "A"

| Ingredient | Parts |
| --- | --- |
| Guanidine Compound | 60–300 |
| Calcium Carbonate | 300 |
| Citric Acid (Anhydrous) | 290 |
| Magnesium Carbonate | 129 |

FORMULATION "B"

| Ingredient | Parts |
| --- | --- |
| Guanidine Compound | 60–300 |
| Citric Acid (Anhydrous) | 1000 |
| Sodium Bicarbonate | 2000 |
| Monocalcium Phosphate | 200 |

FORMULATION "C"

| Ingredient | Parts |
| --- | --- |
| Guanidine Compound | 60–300 |
| Corn Starch | 25–50 |
| Lactose | 25–2000 |
| Magnesium Stearate | 1–5 |

FORMULATION "D"

| Ingredient | Parts |
| --- | --- |
| Guanidine Compound | 60–30 |
| Corn Starch | 25–50 |
| Lactose | 25–200 |
| Talc | 10–50 |
| Silica (Powdered) | 0.1–2 |

FORMULATION "E"

| Ingredient | Parts |
| --- | --- |
| Guanidine Compound | 60–30 |
| Lactose | 65–190 |
| Cellulose | 10–135 |
| Magnesium Stearate | 0.1–5 |

FORMULATION "F"

| Ingredient | Parts |
| --- | --- |
| Guanidine Compound | 60–300 |
| Cellulose | 15–200 |
| Corn Starch | 10–50 |
| Gelatin | 5–35 |
| Stearic Acid | 15 |

FORMULATION "F"

| Ingredient | Parts |
| --- | --- |
| Guanidine Compound | 60–300 |
| Tricalcium Phosphate | 50–150 |
| Corn Starch | 10–50 |
| Acacia | 5–25 |
| Magnesium Stearate | 1–5 |

In each instance, the ingredients in the proportions indicated are milled to a uniform powder, sized, mixed with binder and compressed into tablets.

EXAMPLE VI

Suppositories melting at about 60°F and each having the following composition are produced by compounding the ingredients in the relative proportions indicated and heating the ingredients to about 60°F to effect a solution. The solution is then poured into cooled molds and allowed to cool and solidify.

| Ingredient | Amount |
| --- | --- |
| Guanidine Compound | 0.1 to 1.0 mg |
| Base of lactose, polyethylene glycol, polyethylene glycol 400, polyethylene glycol 4000, polysorbate 80 and glycerine | 1 gram |

EXAMPLE VII

A glosset for sublingual administration was prepared using 60 to 300 mg of guanidine compound disposed in a rapidly disintegrating base formed of starch, lactose, sodium saccharin and talcum.

EXAMPLE VIII

The ingredients of the following compositions were compounded to provide a solution suitable for intravenous administration. In each instance, the ingredients were mixed and warmed to about 50°–60°C with stirring to effect solution. The solution was then sterile filtered, cooled to room temperature, and packaged in sterile vials.

| FORMULATION "H" | |
| --- | --- |
| Ingredient | Amount |
| Guanidine Compound | 10-500 mg |
| Sodium Chloride | 890 mg |
| Water | 99 g |

| FORMULATION "I" | |
| --- | --- |
| Ingredient | Amount |
| Guanidine Compound | 10-500 mg |
| Glucose | 5 g |
| Water | 95 g |

EXAMPLE IX

The ingredients of the following compositions were compounded to provide a solution suitable for intramuscular and subcutaneous formulations administration. In each instance, the ingredients were mixed and warmed to 50°-60°C with stirring to effect solution. The solution was then sterile filtered, cooled to room temperature, and packaged in sterile vials.

| FORMULATION "J" | |
| --- | --- |
| Ingredient | Amount |
| Guanidine Compound | 10-500 mg |
| 16% Aqueous Gelatin Containing 0.5% Phenol | 100 g |

| FORMULATION "K" | |
| --- | --- |
| Ingredient | Amount |
| Guanidine Compound | 10-500 mg |
| Sodium Chloride | 890 g |
| Water | 99 g |

| FORMULATION "L" | |
| --- | --- |
| Ingredient | Amount |
| Guanidine Compound | 10-500 mg |
| Glucose | 5 g |
| Water | 95 g |

| FORMULATION "M" | |
| --- | --- |
| Ingredient | Amount |
| Guanidine Compound | 10-500 mg |
| 10-90% Aqueous Polyethylene Glycol 400 | 100 g |

EXAMPLE X

The guanidine compound is dispersed in a cream vehicle consisting of a water-miscible base of stearic acid, propylene glycol, sorbitol monostearate and mono-oleate, polyoxyethylene sorbitan monostearate with citric acid and methyl and propyl parabens as preservatives. Concentration of the guanidine compound is 0.1 to 50 mg per gram of vehicle.

Alternately, the guanidine compound may be dispersed in corn oil, sesame oil, cotton seed oil, peanut oil, or polyethylene glycols with the addition of appropriate preservatives.

EXAMPLE XI

The vasoconstrictor properties of several representative compounds of this invention were determined pharmacologically using accepted methodology. The heart rate changes in anesthetized dogs who received an intravenous dosage of a guanidine compound as indicated. Throughout the procedure, host blood pressure was monitored by means of an indwelling arterial catheter connected to a pressure transducer, host heart rate was determined from the limb electrocardiogram, and cartoid arterial blood flow was continuously monitored with a flow probe around the artery which probe was connected to an Na electromagnetic flow meter. It will be noted that three standard vasoconstrictors, all current commercial products, were also assayed in this manner and provide a reference base. The test compounds are coded in Table I and the data is reported in subsequent tables below.

TABLE I

| Test Compound Code | Chemical Name |
| --- | --- |
| K | Phenyl guanidine nitrate |
| L | 3'-Hydroxyphenyl guanidine hydrochloride |
| M | 2'-Methylphenyl guanidine nitrate |
| N | 3',4'-Dichlorophenyl guanidine hydrochloride |

TABLE II

Heart Rate Changes in Anesthetized Dogs

| Test Compound | Dose (mg/Kg. i.v.) | | |
| --- | --- | --- | --- |
| | 0.01 | 0.1 | 1.0 |
| K | 0 | 0 | 0 |
| L | 0 | – | – |
| M | 0 | 0 | – |
| N | – | – | – |
| Naphazoline | – | – | + |
| Phenylephrine | – | + | + |
| Phenylpropanolamine | 0 | +– | – |

Rating Scale:
—Decrease in heart rate
O No change in heart rate
+Increase in heart rate

EXAMPLE XII

Additional data was obtained for each representative compound by measuring the rise in mean arterial blood pressure after intravenous administration to an anesthetized dog.

The scale employed to evaluate the results is shown in Table III, and the test data is recorded in Table IV, using the code for test compounds set forth in Table I of Example XI.

TABLE III

| Activity Rating | Pressure Rise in mm Hg |
| --- | --- |
| 0 | 0 – 3 |
| 1 | 4 – 10 |
| 2 | 11 – 25 |
| 3 | 26 – 50 |
| 4 | 51 – 75 |
| 5 | 75 |

TABLE IV

Activity Rating for Test Compounds

| Test Compound | Dose (mg/Kg. i.v.) | | |
| --- | --- | --- | --- |
| | 0.01 | 0.1 | 1.0 |
| K | 0 | 0 | 3 |
| L | 0 | 2 | 5 |
| M | 0 | 0 | 2 |
| N | 4 | 5 | 5 |
| Naphazoline | 3 | 4 | 4 |
| Phenylephrine | 3 | 5 | 5 |
| Phenylpropanolamine | 0 | 3 | 5 |

EXAMPLE XIII

An aqueous solution was prepared containing 3',4'-dichlorophenyl guanidine hydrochloride and suitable for use with the nose and eyes to effect decongestion of the mucus membranes of these organs. The solution was stable, physiologically isotonic and had a pH in the range of 6 to 7.

The formulation is shown below. The sodium phosphate salts comprise a buffer system to maintain the pH at about 6.5 and sodium bisulfite is used as an antioxidant. Sodium chloride provides the desired isotonicity and thimersol as a preservative which protects the solution from bacterial and mold contamination.

| FORMULATION "N" | |
|---|---|
| Ingredient | Wt.% |
| 3',4'-Dichlorophenyl guanidine hydrochloride | 2.00 |
| Monbasic Sodium Phosphate | 0.10 |
| Dibasic Sodium Phosphate | 0.12 |
| Sodium Bisulfite | 0.20 |
| Sodium Chloride | 0.15 |
| Merthiolate Sodium (Thimerosal) | 0.01 |
| Water | 97.42 |

Especially preferred in the practice of this invention are the species compounds and salts denominated 3',4'-dichlorophenyl quanidine hydrochloride; 3'-hydroxyphenyl guanidine hydrochloride; and 2'-methylphenyl guanidine nitrate; and their corresponding bases.

From the foregoing, it becomes apparent that the invention herein described and illustrated fulfills all of our objectives, express and implied, in a remarkably unexpected fashion and that we have developed new and useful compounds, pharmaceutical compositions and therapeutic methods for providing vasoconstriction in hosts requiring such therapy.

What we claim is:

1. A pharmaceutical preparation for providing vasoconstrictive therapy comprising a pharmaceutically acceptable carrier and an effective amount of a phenylguanidine compound, or a non-toxic acid addition salt thereof, said compound having the formula:

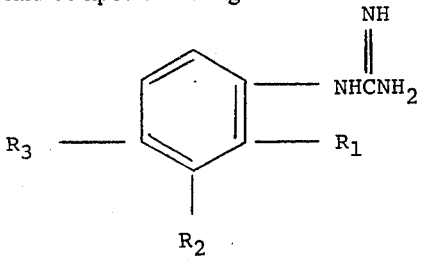

wherein: $R_1$ is hydrogen and $R_2$ and $R_3$ are chloro; or $R_1$ and $R_4$ are hydrogen and $R_3$ is hydroxy; or $R_1$ is methyl and $R_2$ and $R_3$ are hydrogen.

2. A preparation according to claim 1 in which said compound is denominated 3',4'-dichlorophenyl guanidine.

3. A preparation according to claim 1 in which said compound is denominated 3'-hydroxyphenyl guanidine.

4. A preparation according to claim 1 in which said acid addition salt is 3',4'-dichlorophenyl guanidine hydrochloride.

5. A preparation according to claim 1 in which said acid addition salt is 3'-hydroxyphenyl guanidine hydrochloride.

6. A preparation according to claim 1 in which said compound is 2'-methylphenyl guanidine.

7. A pharmaceutical preparation according to claim 1 in a unit dosage form selected from the group consisting of a tablet, a capsule, a packet, a lozenge, a glosset, a sterile solution, a suspension, an emulsion, an ointment, and a suppository.

8. A method of producing vasoconstriction in a host in need thereof which comprises administering to said host a sufficient amount of a phenylguanidine compound, or a non-toxic acid addition salt thereof, to provide said host a dose of the said compound of from about 1 mg. to about 5 mg. per kilogram of host body weight, said compound having the formula:

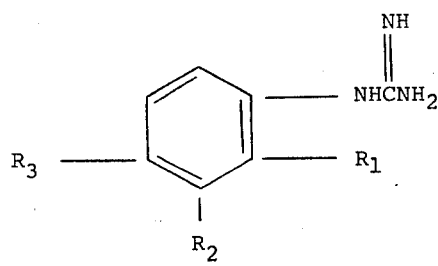

wherein: $R_1$ is hydrogen or alkyl having 1–4 carbon atoms; $R_2$ is hydrogen, hydroxy, chloro, fluoro or bromo; and $R_3$ is hydrogen or the same as $R_2$ when $R_2$ is chloro, bromo or fluoro.

9. A method according to claim 8 in which said guanidine is denominated 3',4'-dichlorophenyl guanidine.

10. A method according to claim 8 in which said guanidine is denominated 3'-hydroxyphenyl guanidine.

11. A method according to claim 8 in which said guanidine is delivered as a hydrochloride salt.

12. A method according to claim 8 in which said compound is 2'-methylphenyl guanidine.

* * * * *